(12) United States Patent
Parisi et al.

(10) Patent No.: US 8,858,643 B2
(45) Date of Patent: Oct. 14, 2014

(54) TIBIAL BEARING COMPONENT FOR A KNEE PROSTHESIS WITH IMPROVED ARTICULAR CHARACTERISTICS

(75) Inventors: Raymond C. Parisi, Wakarusa, IN (US); Abraham P. Habegger, Warsaw, IN (US); Peter S. Walker, New York, NY (US); Jeff C. Blaylock, Fort Wayne, IN (US); Kathleen P. Macke, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 13/459,037

(22) Filed: Apr. 27, 2012

(65) Prior Publication Data

US 2013/0131816 A1 May 23, 2013

Related U.S. Application Data

(60) Provisional application No. 61/561,657, filed on Nov. 18, 2011, provisional application No. 61/577,293, filed on Dec. 19, 2011, provisional application No. 61/592,576, filed on Jan. 30, 2012, provisional application No. 61/621,361, filed on Apr. 6, 2012, provisional application No. 61/621,363, filed on Apr. 6, 2012, provisional application No. 61/621,364, filed on Apr. 6, 2012, provisional application No. 61/621,366, filed on Apr. 6, 2012.

(51) Int. Cl.
*A61F 2/38* (2006.01)
*A61F 2/30* (2006.01)

(52) U.S. Cl.
CPC ....... *A61F 2/389* (2013.01); *A61F 2002/30616* (2013.01); *A61F 2/3868* (2013.01); *A61F 2/3886* (2013.01)
USPC .................. 623/20.32; 623/20.28; 623/20.31

(58) Field of Classification Search
USPC .......... 623/20.14, 20.15, 20.16, 20.17, 20.18, 623/20.19, 20.2, 20.21, 20.22, 20.23, 20.24, 623/20.25, 20.26, 20.27, 20.28, 20.29, 20.3, 623/20.31, 20.32, 20.33, 20.34, 20.35, 623/20.36
See application file for complete search history.

(56) References Cited

U.S. PATENT DOCUMENTS

| 5,047,057 A | 9/1991 | Lawes |
| 5,059,216 A | 10/1991 | Winters |

(Continued)

FOREIGN PATENT DOCUMENTS

| CN | 101214175 A | 7/2008 |
| EP | 0636353 A1 | 2/1995 |

(Continued)

OTHER PUBLICATIONS

International Search Report and Written Opinion mailed Jun. 8, 2012 from the International Searching Authority in related International Application No. PCT/US2012/035679.

(Continued)

*Primary Examiner* — Marcia Hoffman
(74) *Attorney, Agent, or Firm* — Schwegmen Lundberg & Woessner, P.A.

(57) ABSTRACT

An orthopaedic knee prosthesis includes a tibial bearing component with surface features which operate to protect adjacent soft tissues of the natural knee throughout a wide range of flexion. More particularly, the tibial bearing component provides an anterior relief space disposed between the dished lateral and medial articular compartments, in which the relief space is convex as viewed from a sagittal perspective across the medial/lateral extent of the relief space.

23 Claims, 10 Drawing Sheets

(56) References Cited

U.S. PATENT DOCUMENTS

| | | |
|---|---|---|
| 5,171,283 A | 12/1992 | Pappas et al. |
| 5,192,328 A | 3/1993 | Winters |
| 5,219,362 A | 6/1993 | Tuke et al. |
| 5,282,870 A | 2/1994 | Moser et al. |
| 5,387,240 A | 2/1995 | Pottenger et al. |
| 5,413,604 A | 5/1995 | Hodge |
| 5,609,639 A | 3/1997 | Walker |
| 5,609,643 A | 3/1997 | Colleran et al. |
| 5,658,342 A | 8/1997 | Draganich et al. |
| 6,013,103 A | 1/2000 | Kaufman et al. |
| 6,068,658 A | 5/2000 | Insall et al. |
| 6,080,195 A | 6/2000 | Colleran et al. |
| 6,102,954 A | 8/2000 | Albrektsson et al. |
| 6,203,576 B1 | 3/2001 | Afriat et al. |
| 6,210,443 B1 | 4/2001 | Marceaux et al. |
| 6,325,828 B1 | 12/2001 | Dennis et al. |
| 6,406,497 B2 | 6/2002 | Takei et al. |
| 6,428,577 B1 | 8/2002 | Evans |
| 6,491,726 B2 | 12/2002 | Pappas |
| 6,558,426 B1 | 5/2003 | Masini |
| 6,660,039 B1 | 12/2003 | Evans et al. |
| 7,081,137 B1 | 7/2006 | Servidio |
| 7,160,330 B2 | 1/2007 | Axelson, Jr. et al. |
| 7,261,740 B2 | 8/2007 | Tuttle |
| 7,264,635 B2 | 9/2007 | Suguro |
| 7,309,362 B2 | 12/2007 | Yasuda et al. |
| 7,326,252 B2 | 2/2008 | Otto et al. |
| 7,351,263 B2 | 4/2008 | Afriat |
| 7,413,577 B1 | 8/2008 | Servidio |
| 7,625,407 B2 | 12/2009 | Akizuki |
| 7,635,390 B1 | 12/2009 | Bonutti |
| 7,678,152 B2 | 3/2010 | Suguro et al. |
| 7,776,085 B2 | 8/2010 | Bernero et al. |
| 2005/0055102 A1 | 3/2005 | Tornier et al. |
| 2005/0096747 A1 | 5/2005 | Tuttle et al. |
| 2005/0197710 A1 | 9/2005 | Naegerl |
| 2005/0209701 A1 | 9/2005 | Suguro et al. |
| 2006/0004460 A1* | 1/2006 | Engh et al. ............... 623/20.21 |
| 2006/0265080 A1 | 11/2006 | McMinn et al. |
| 2007/0185581 A1 | 8/2007 | Akizuki et al. |
| 2007/0233269 A1 | 10/2007 | Steines et al. |
| 2008/0119940 A1 | 5/2008 | Otto et al. |
| 2008/0161918 A1 | 7/2008 | Fankhauser et al. |
| 2008/0243258 A1 | 10/2008 | Sancheti |
| 2008/0288080 A1 | 11/2008 | Sancheti |
| 2008/0300689 A1* | 12/2008 | Mc Kinnon et al. ....... 623/20.18 |
| 2008/0300690 A1 | 12/2008 | Burstein et al. |
| 2009/0043395 A1 | 2/2009 | Hotokebuchi et al. |
| 2009/0210066 A1 | 8/2009 | Jasty |
| 2009/0222103 A1 | 9/2009 | Fitz et al. |
| 2009/0265011 A1 | 10/2009 | Mandell |
| 2009/0265013 A1 | 10/2009 | Mandell |
| 2009/0319048 A1 | 12/2009 | Shah et al. |
| 2009/0319049 A1 | 12/2009 | Shah et al. |
| 2009/0326663 A1 | 12/2009 | Dun |
| 2009/0326665 A1 | 12/2009 | Wyss et al. |
| 2009/0326666 A1 | 12/2009 | Wyss et al. |
| 2009/0326668 A1 | 12/2009 | Dun |
| 2010/0016976 A1 | 1/2010 | Siebel |
| 2010/0016979 A1 | 1/2010 | Wyss et al. |
| 2010/0036499 A1 | 2/2010 | Pinskerova |
| 2010/0036500 A1 | 2/2010 | Heldreth et al. |
| 2010/0191341 A1 | 7/2010 | Byrd |
| 2010/0262253 A1 | 10/2010 | Cipolletti et al. |
| 2010/0286788 A1 | 11/2010 | Komistek |
| 2010/0305708 A1 | 12/2010 | Lang |
| 2010/0329530 A1 | 12/2010 | Lang et al. |
| 2011/0022179 A1 | 1/2011 | Andriacchi et al. |
| 2011/0029091 A1 | 2/2011 | Bojarski et al. |
| 2011/0082558 A1 | 4/2011 | Kim et al. |
| 2011/0125278 A1 | 5/2011 | Bercovy et al. |
| 2011/0144760 A1 | 6/2011 | Wong et al. |
| 2011/0251695 A1 | 10/2011 | Lenz et al. |

| | | |
|---|---|---|
| 2013/0131817 A1 | 5/2013 | Parisi et al. |
| 2013/0131818 A1 | 5/2013 | Parisi et al. |
| 2013/0131819 A1 | 5/2013 | Parisi et al. |

FOREIGN PATENT DOCUMENTS

| | | |
|---|---|---|
| EP | 0592750 B1 | 1/1999 |
| EP | 1025818 A2 | 8/2000 |
| EP | 1378216 A2 | 1/2004 |
| EP | 1477143 A1 | 11/2004 |
| EP | 1568336 A1 | 8/2005 |
| EP | 1719478 A2 | 11/2006 |
| EP | 1722721 A1 | 11/2006 |
| EP | 1354571 B1 | 6/2007 |
| EP | 1604623 B1 | 6/2008 |
| EP | 0927009 B1 | 1/2009 |
| EP | 1696835 B1 | 2/2009 |
| EP | 1591082 B1 | 9/2009 |
| EP | 2140838 A2 | 1/2010 |
| EP | 2143403 A1 | 1/2010 |
| EP | 1555962 B1 | 2/2011 |
| EP | 2324799 A2 | 5/2011 |
| EP | 2335654 A1 | 6/2011 |
| FR | 2852819 A1 | 10/2004 |
| JP | 2004166802 A | 6/2004 |
| WO | WO-9514446 A1 | 6/1995 |
| WO | WO-2004058108 A1 | 7/2004 |
| WO | WO-2005051240 A1 | 6/2005 |
| WO | WO-2005122967 A1 | 12/2005 |
| WO | WO-2006058057 A2 | 6/2006 |
| WO | WO-2006092167 A1 | 9/2006 |
| WO | WO-2007109641 A2 | 9/2007 |
| WO | WO-2009088235 A2 | 7/2009 |
| WO | WO-2009088236 A2 | 7/2009 |
| WO | WO-2009088238 A2 | 7/2009 |
| WO | WO-2009105495 A1 | 8/2009 |
| WO | WO-2010001010 A1 | 1/2010 |
| WO | WO-2011072235 A2 | 6/2011 |
| WO | WO-2012112698 A2 | 8/2012 |
| WO | WO-2013074142 A1 | 5/2013 |
| WO | WO-2013074143 A1 | 5/2013 |
| WO | WO-2013074144 A1 | 5/2013 |
| WO | WO-2013074145 A1 | 5/2013 |

OTHER PUBLICATIONS

Zimmer LPS-Flex Fixed Bearing Knee Surgical Technique, Zimmer, Inc. 2004, 2007, 2008.

Zimmer NexGen Complete Knee Solution Surgical Technique for the CR-Flex Fixed Bearing Knee, Zimmer, Inc. 2003.

Zimmer NexGen Complete Knee Solution Extramedullary/Intramedullary Tibial Resector Surgical Technique, Zimmer, Inc. 2000, 2008, 2009.

"U.S. Appl. No. 13/459,041, Preliminary Amendment mailed Apr. 27, 2012", 7 pgs.

"U.S. Appl. No. 13/459,048, Preliminary Amendment filed Apr. 27, 2012", 7 pgs.

"U.S. Appl. No. 13/459,056, Preliminary Amendment filed Apr. 27, 2012", 7 pgs.

"U.S. Appl. No. 13/459,056, Response filed Apr. 8, 2013 to Restriction Requirement mailed Mar. 6, 2013", 15 pgs.

"U.S. Appl. No. 13/459,056, Restriction Requirement mailed Mar. 6, 2013", 6 pgs.

"Bi-Cruciate Stabilized Knee System", Design Rationale, Smith & Nephew Journal, (2006), 20 pgs.

"Gender Solutions Natural Knee Flex System: Because Men and Women are Different", Zimmer, Inc., (2007, 2009), 6 pg.

"Gender Solutions Natural Knee Flex System: Surgical Technique", Zimmer, Inc., (2007, 2008, 2009), 36 pgs.

"International Application Serial No. PCT/US2012/035680, Search Report mailed Oct. 9. 2012", 7 pgs.

"International Application Serial No. PCT/US2012/035680, Written Opinion mailed Oct. 9, 2012", 11 pgs.

"International Application Serial No. PCT/US2012/035683, International Search Report and Written Opinion mailed Jun. 5, 2012", 12 pgs.

(56) References Cited

OTHER PUBLICATIONS

"International Application Serial No. PCT/US2012/035684, International Search Report mailed Aug. 8, 2012", 9 pgs.

"International Application Serial No. PCT/US2012/035684, Written Opinion mailed Jun. 8, 2012", 12 pgs.

"Natural-Knee II Primary System Surgical Technique", Zimmer, Inc., (2005), 48 pgs.

Hofmann, Aaron A, et al., "Posterior Stabilization in Total Knee Arthroplasty with Use of an Ultracongruent Polyethylene", The Journal of Arthroplasty vol. 15, No. 5, (2000), 576-583.

"U.S. Appl. No. 13/459,041, Non Final Office Action mailed Jan. 15, 2014", 16 pgs.

"U.S. Appl. No. 13/459,041, Response filed Sep. 23, 2013 to Restriction Requirement mailed Jul. 25, 2013", 18 pgs.

"U.S. Appl. No. 13/459,041, Restriction Requirement mailed Jul. 25, 2013", 9 pgs.

"U.S. Appl. No. 13/459,048, Non Final Office Action mailed Jul. 11, 2013", 6 pgs.

"U.S. Appl. No. 13/459,048, Notice of Allowance mailed Nov. 26, 2013", 10 pgs.

"U.S. Appl. No. 13/459,048, Response filed Nov. 11, 2013 to Non-Final Office Action mailed Jul. 11, 2013", 16 pgs.

"U.S. Appl. No. 13/459,056, Examiner Interview Summary mailed Dec. 26, 2013", 3 pgs.

"U.S. Appl. No. 13/459,056, Non Final Office Action mailed Jul. 25, 2013", 11 pgs.

"U.S. Appl. No. 13/459,056, Notice of Allowance mailed Feb. 20, 2014", 5 pgs.

"U.S. Appl. No. 13/459,056, Response filed Jan. 24, 2014 to Non-Final office Action mailed Jul. 25, 2013", 27 pgs.

\* cited by examiner

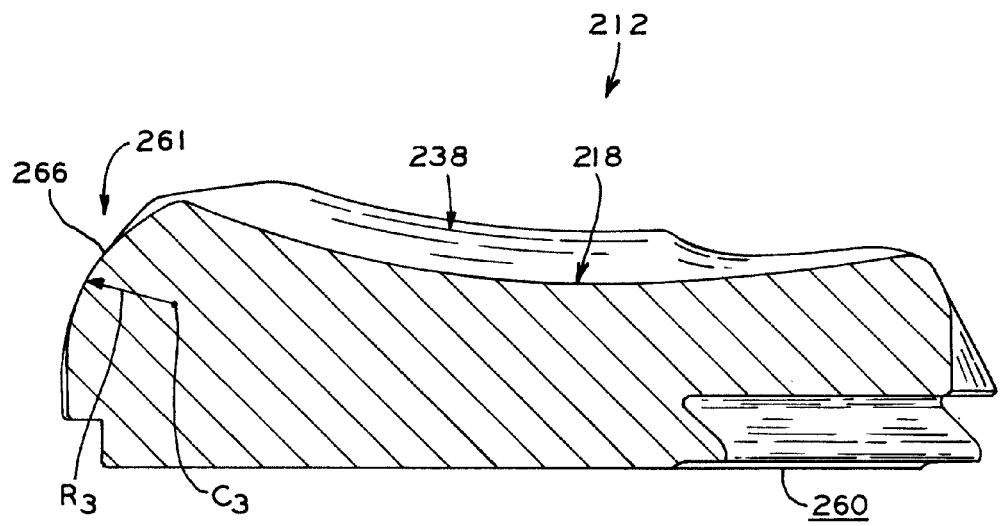
FIG_5
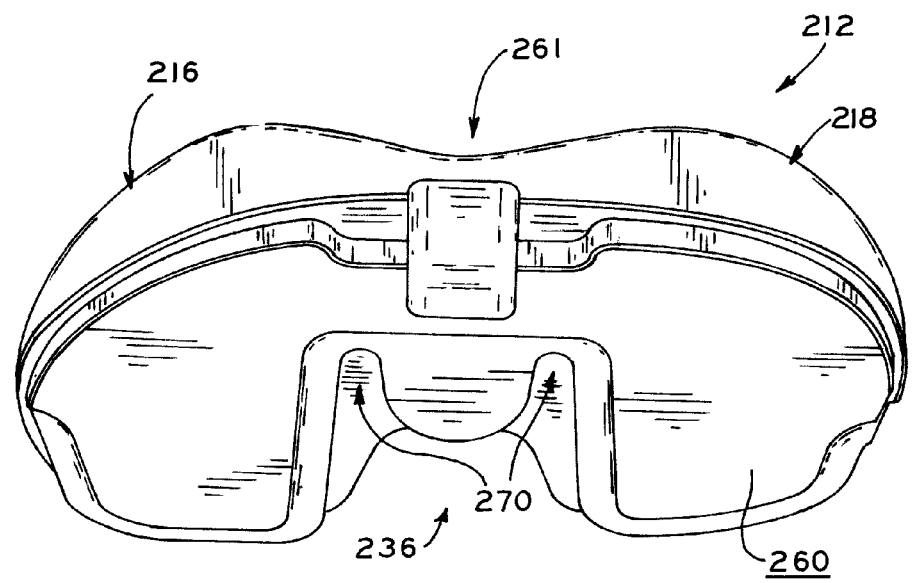
FIG_6

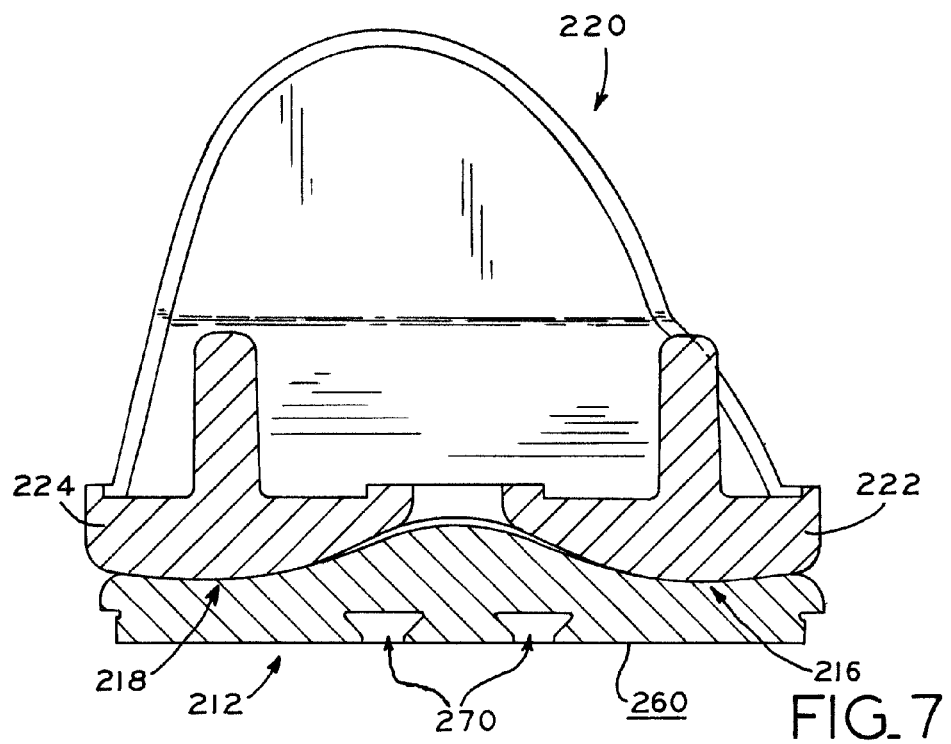
FIG_7
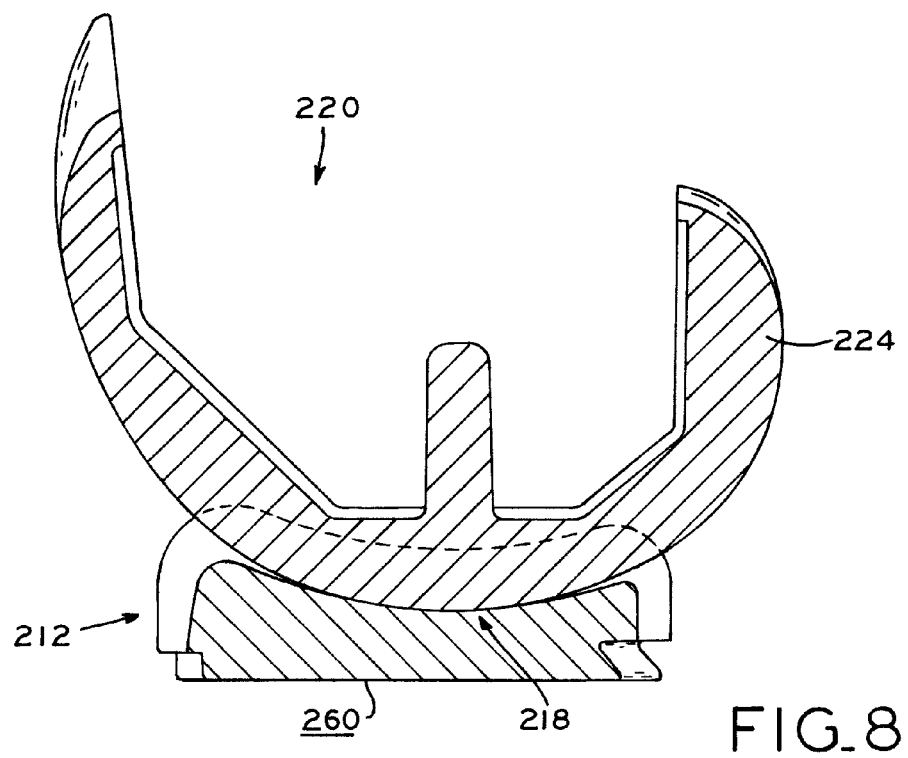
FIG_8

FIG_11

TIBIAL BEARING COMPONENT FOR A KNEE PROSTHESIS WITH IMPROVED ARTICULAR CHARACTERISTICS

CROSS-REFERENCE TO RELATED APPLICATIONS

This application claims the benefit under Title 35, U.S.C. §119(e) of U.S. Provisional Patent Application Ser. No. 61/561,657 filed Nov. 18, 2011, U.S. Provisional Patent Application Ser. No. 61/577,293 filed Dec. 19, 2011, U.S. Provisional Patent Application Ser. No. 61/592,576 filed Jan. 30, 2012, U.S. Provisional Patent Application Ser. No. 61/621,361 filed Apr. 6, 2012, U.S. Provisional Patent Application Ser. No. 61/621,363 filed Apr. 6, 2012, U.S. Provisional Patent Application Ser. No. 61/621,364 filed Apr. 6, 2012, and U.S. Provisional Patent Application Ser. No. 61/621,366 filed Apr. 6, 2012, each entitled TIBIAL BEARING COMPONENT FOR A KNEE PROSTHESIS WITH IMPROVED ARTICULAR CHARACTERISTICS, the entire disclosures of which are hereby expressly incorporated by reference herein.

BACKGROUND

1. Technical Field

The present disclosure relates to orthopaedic prostheses and, specifically, to articular tibial components in a knee prosthesis.

2. Description of the Related Art

Orthopaedic prostheses are commonly utilized to repair and/or replace damaged bone and tissue in the human body. For a damaged knee, a knee prosthesis may be implanted using a tibial baseplate, a tibial bearing component, and a distal femoral component. The tibial baseplate is affixed to a proximal end of the patient's tibia, which is typically resected to accept the baseplate. The femoral component is implanted on a distal end of the patient's femur, which is also typically resected to accept the femoral component. The tibial bearing component is placed between the tibial baseplate and femoral component, and may be fixed upon or slidably coupled to the tibial baseplate.

The tibial bearing component, which may also be referred to as a tibial insert or meniscal component, provides an articular surface which interacts with the adjacent femur or femoral component during extension and flexion of the knee.

Prior art tibial bearing components have included anterior relief spaces which are at least partially concave along their medial/lateral extents (i.e., as viewed from a coronal/transverse perspective), and at least partially convex as viewed from a sagittal perspective. However, these prior art anterior relief spaces have not been convex across the entire anterior/posterior span, instead having one or more flat expanses of material in the anterior relief space. Further, as a result of these flat expanses of material, the radii defined by the sagittally convex portions of the prior art anterior relief spaces are substantially less than 5 mm.

The features and geometry of the articular surface influences the interaction with the tibial bearing component and the surrounding soft tissues after implantation. Substantial design efforts have previously focused on providing knee prosthesis components which protect the natural tissues of the knee during the in vivo use of the components.

SUMMARY

The present disclosure provides an orthopaedic knee prosthesis including a tibial bearing component with surface features which operate to protect adjacent soft tissues of the natural knee throughout a wide range of flexion. More particularly, the tibial bearing component provides an anterior relief space disposed between the dished lateral and medial articular compartments, in which the relief space is convex as viewed from a sagittal perspective across the medial/lateral extent of the relief space.

According to one embodiment thereof, the present invention provides a tibial bearing component for articulation with femoral condyles, the tibial bearing component defining a tibial bearing component coordinate system comprising: a bearing component transverse plane extending along a medial/lateral direction and an anterior/posterior direction; a bearing component coronal plane extending along a proximal/distal direction and the medial/lateral direction, the bearing component coronal plane perpendicular to the bearing component transverse plane; and a bearing component sagittal plane extending along the anterior/posterior direction and the proximal/distal direction, the bearing component sagittal plane perpendicular to the bearing component transverse plane and the bearing component coronal plane, the tibial bearing component comprising: an articular surface and an opposing distal surface, the distal surface parallel to the bearing component transverse plane, the articular surface including medial and lateral dished articular compartments sized and shaped for articulation with the femoral condyles, the medial and lateral dished articular compartments separated from one another by the bearing component sagittal plane, the articular and distal surfaces bounded by a tibial bearing periphery, an anterior relief space situated at a medial/lateral location between the medial and lateral dished articular surfaces to define a medial/lateral span, the anterior relief space situated adjacent to an anterior edge of the tibial bearing periphery and extending posteriorly from the anterior edge across an anterior/posterior span, the medial/lateral span of the anterior relief space comprising a plurality of sagittal cross-sectional profiles each extending from a posterior edge of the anterior relief space to an anterior edge of the anterior relief space, each of the plurality of sagittal cross-sectional profiles defining a convex sagittal curve extending from the posterior edge to the anterior edge of the anterior relief space.

According to another embodiment thereof, the present invention provides a tibial bearing component for articulation with femoral condyles, the tibial bearing component defining a tibial bearing component coordinate system comprising: a bearing component transverse plane extending along a medial/lateral direction and an anterior/posterior direction; a bearing component coronal plane extending along a proximal/distal direction and the medial/lateral direction, the bearing component coronal plane perpendicular to the bearing component transverse plane; and a bearing component sagittal plane extending along the anterior/posterior direction and the proximal/distal direction, the bearing component sagittal plane perpendicular to the bearing component transverse plane and the bearing component coronal plane, the tibial bearing component comprising: an articular surface and an opposing distal surface, the distal surface parallel to the bearing component transverse plane, the articular surface including medial and lateral dished articular compartments sized and shaped for articulation with the femoral condyles, the medial and lateral dished articular compartments separated from one another by the bearing component sagittal plane, the articular and distal surfaces bounded by a tibial bearing periphery, an anterior relief space situated at a medial/lateral location between the medial and lateral dished articular surfaces to define a medial/lateral span, the anterior relief space situated adjacent to an anterior edge of the tibial bearing periphery and extending posteriorly from the anterior edge across an anterior/posterior span, the medial/lateral span of the anterior relief space comprising a plurality of sagittal cross-sectional profiles, each of the plurality of sagittal cross-sectional profiles defining a convex sagittal curve defining a sagittal curve radius of at least 5 mm.

BRIEF DESCRIPTION OF THE DRAWINGS

The above mentioned and other features and advantages of this disclosure, and the manner of attaining them, will become more apparent and the invention itself will be better understood by reference to the following description of embodiments of the invention taken in conjunction with the accompanying drawings, wherein:

FIG. 5 is another elevation, cross-sectional view of the tibial bearing component shown in FIG. 1, taken along the line 5-5 of FIGS. 1 and 2;

FIG. 6 is bottom, perspective view of the tibial bearing component shown in FIG. 1, in which the anterior relief space of the tibial bearing component has coronal and transverse concavity; and FIG. 7 is an elevation, cross-sectional view of the tibial bearing component shown in FIG. 1, together with a femoral component made in accordance with the present disclosure, in which the cross-section is taken in a coronal plane passing through the distal-most points of the tibial bearing component;

FIG. 8 is an elevation, cross-sectional view of the tibial bearing and femoral components shown in FIG. 7, in which the cross-section is taken in a sagittal plane passing through the lateral distal-most point of the tibial bearing component;

Corresponding reference characters indicate corresponding parts throughout the several views. The exemplifications set out herein illustrate exemplary embodiments of the invention, and such exemplifications are not to be construed as limiting the scope of the invention in any manner.

DETAILED DESCRIPTION

The present disclosure provides tibial bearing components for a knee prosthesis in which the bearing components have a rounded, sagittally convex anterior relief space which functions to protect soft tissues during knee articulation.

As used herein, "proximal" refers to a direction generally toward the torso of a patient, and "distal" refers to the opposite direction of proximal, i.e., away from the torso of a patient. "Anterior" refers to a direction generally toward the front of a patient or knee, and "posterior" refers to the opposite direction of anterior, i.e., toward the back of the patient or knee. In the context of a prosthesis alone, such directions generally correspond to the orientation of the prosthesis after implantation, such that a proximal portion of the prosthesis is that portion which will ordinarily be closest to the torso of the patient, the anterior portion closest to the front of the patient's knee, etc.

Figure 9:
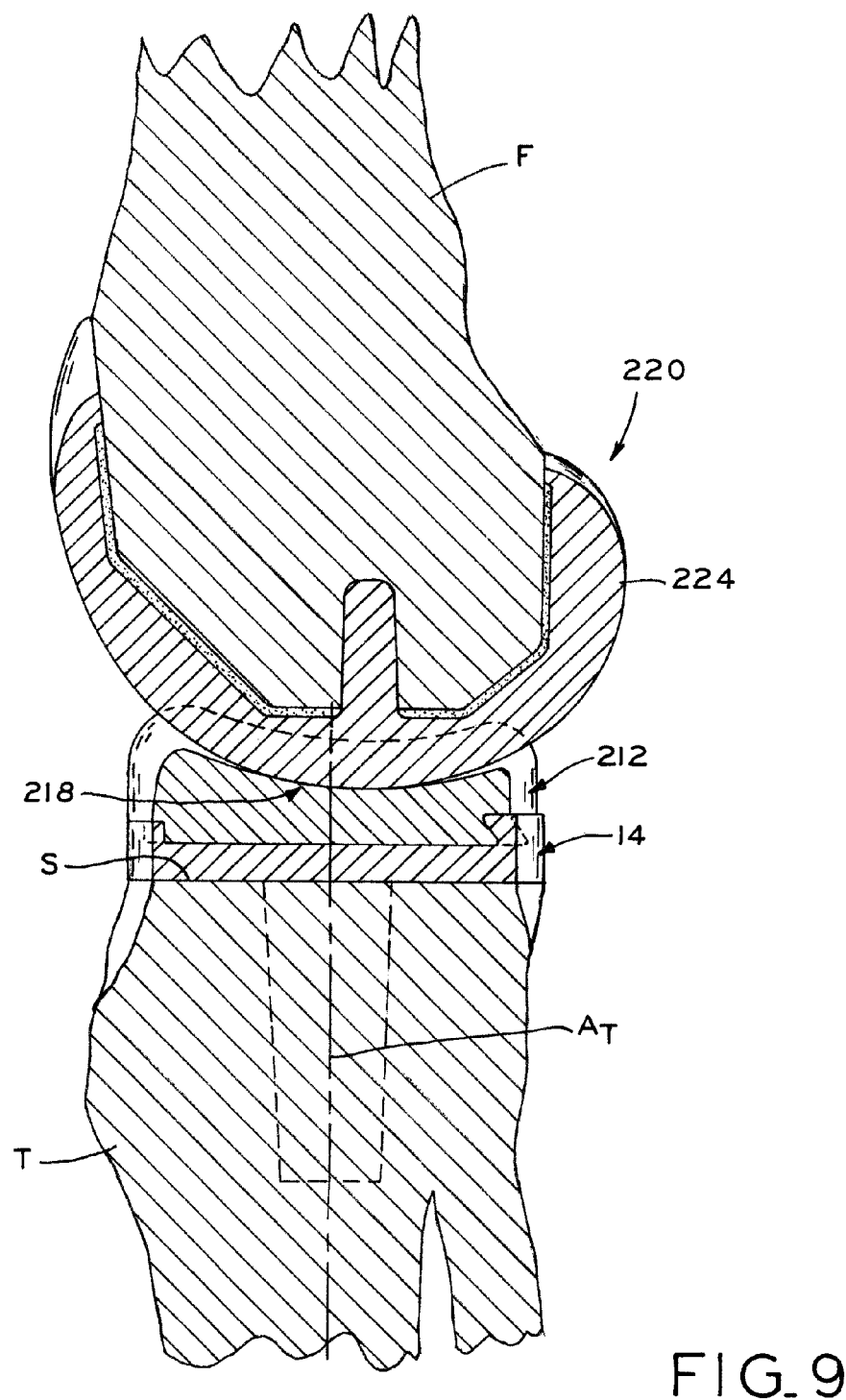
FIG. 9 is an elevation, cross-sectional view of the tibial bearing and femoral components shown in FIGS. 7 and 8, with the tibial bearing component implanted onto a tibia and the femoral component implanted onto a femur.

Similarly, knee prostheses in accordance with the present disclosure may be referred to in the context of a coordinate system including transverse, coronal and sagittal planes of the component. Upon implantation of the prosthesis and with a patient in a standing position, a transverse plane of the knee prosthesis is generally parallel to an anatomic transverse plane, i.e., the transverse plane of the knee prosthesis is inclusive of imaginary vectors extending along medial/lateral and anterior/posterior directions. However, in some instances the bearing component transverse plane will be slightly angled with respect to the anatomic transverse plane, such as when the proximal surface of the resected tibia T (FIG. 9) defines an anteroposterior slope. In FIG. 9, tibia T is shown with no such anteroposterior slope, in that proximal resected surface S of tibia T is normal to anatomic axis $A_T$ of tibia T. In some instances, a surgeon will choose to resect tibia T such that proximal resected surface S elevates the anterior portion of tibial bearing component 212 (and of tibial baseplate 14) with respect to the posterior portion thereof. Where such anteroposterior slope is imparted, the bearing component transverse plane will be angled with respect to the anatomic transverse plane, with the magnitude of such angle being approximately equal to the magnitude of the anteroposterior slope.

Coronal and sagittal planes of the knee prosthesis are also generally parallel to the coronal and sagittal anatomic planes in a similar fashion. Thus, a coronal plane of the prosthesis is inclusive of vectors extending along proximal/distal and medial/lateral directions, and a sagittal plane is inclusive of vectors extending along anterior/posterior and proximal/distal directions. As with the relationship between the anatomic and bearing component transverse planes discussed above, it is appreciated that small angles may be formed between the bearing component sagittal and coronal planes and the corresponding anatomic sagittal and coronal planes depending upon the surgical implantation method. For example, creation of an anteroposterior slope defined by resected surface S of tibia T (FIG. 9) will angle the bearing component coronal plane with respect to the anatomic coronal plane, while alteration of the resected surface S for correction of a varus or valgus deformity will angle the bearing component sagittal plane with respect to the anatomic sagittal plane.

As with anatomic planes, the sagittal, coronal and transverse planes defined by the knee prosthesis are mutually perpendicular to one another. For purposes of the present disclosure, reference to sagittal, coronal and transverse planes is with respect to the present knee prosthesis unless otherwise specified.

The embodiments shown and described herein illustrate components for a left knee prosthesis. Right and left knee prosthesis configurations are mirror images of one another about a sagittal plane. Thus, it will be appreciated that the aspects of the prosthesis described herein are equally applicable to a left or right knee configuration.

In one exemplary embodiment shown in FIGS. 1-5, a "cruciate retaining" (CR) design is illustrated in tibial bearing component 212. CR designs are generally used in surgical procedures which retain the PCL, thereby allowing the natural anatomical structures of the knee to provide posterior stabilization. For example, referring to FIG. 1, posterior cutout 236 is sized and positioned to accommodate the PCL upon implantation of tibial bearing component 212. Intercompartmental ridge 238 extends anteroposteriorly from posterior 236 cutout to anterior relief space 261, and provides medial/lateral stabilization of the knee. As described in detail below, anterior relief space 261 extends from the anterior end of intercondylar ridge 238 to an anterior edge of the periphery of tibial bearing component 212. Thus, the intercondylar ridge defined by intercompartmental ridge 238 is disposed between said medial and lateral dished articular compartments and occupies the available anterior/posterior space therebetween.

Tibial bearing component 212 may also take the form of an "ultra congruent" (UC) design, which utilizes very high congruence between the tibial bearing compartments and femoral condyles to provide prosthesis stability, particularly with respect to anterior/posterior relative motion. This high congruence allows UC designs to be used for patients whose PCL is resected.

"Congruence," in the context of knee prostheses, sometimes also referred to as conformity, refers to the similarity of curvature between the convex femoral condyles and the correspondingly concave tibial articular compartments. A convex surface may be considered to be highly conforming with a corresponding concave surface where the two surfaces have similar or identical convex and concave geometries, such that the convex surface "nests" or tightly interfits with the concave surface. For example, a hemisphere having a radius perfectly conforms (i.e., defines high conformity) with a corresponding hemispherical cavity having the same radius. Conversely, the hemisphere would have low conformity with an adjacent flat or convex surface.

For both CR and UC prosthesis designs, femoral component 220 (FIGS. 7 and 8) may be provided to articulate with tibial bearing component 212. In FIG. 9, femoral component 220 is shown implanted onto a resected distal portion of femur F and tibial component 212 is shown implanted onto a resected proximal portion of tibia T, with components 212, 220 in a "full extension" orientation. Femoral component 220 lacks a femoral cam (such as cam 40, described below), and therefore defines an uninterrupted intercondylar space. Unlike the cam/spine interaction indicative of a posterior-stabilized prosthesis described below, intercondylar ridge 238 lacks a posterior face designed to articulate with femoral component 220, so no femoral cam is needed.

Figure 10:
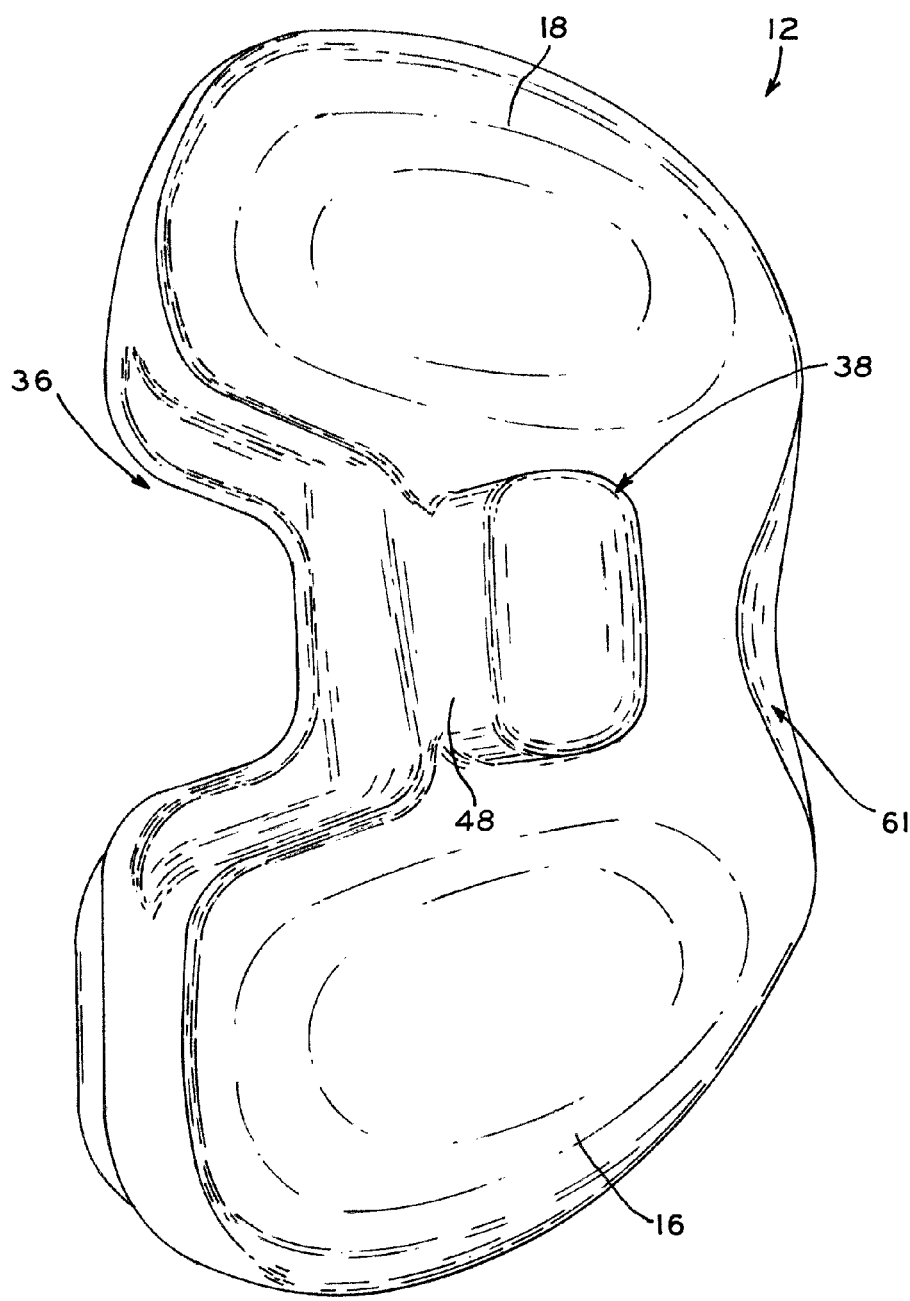
FIG. 10 is a top perspective view of a posterior stabilized (PS) tibial bearing component and baseplate in accordance with the present disclosure.
Figure 11:
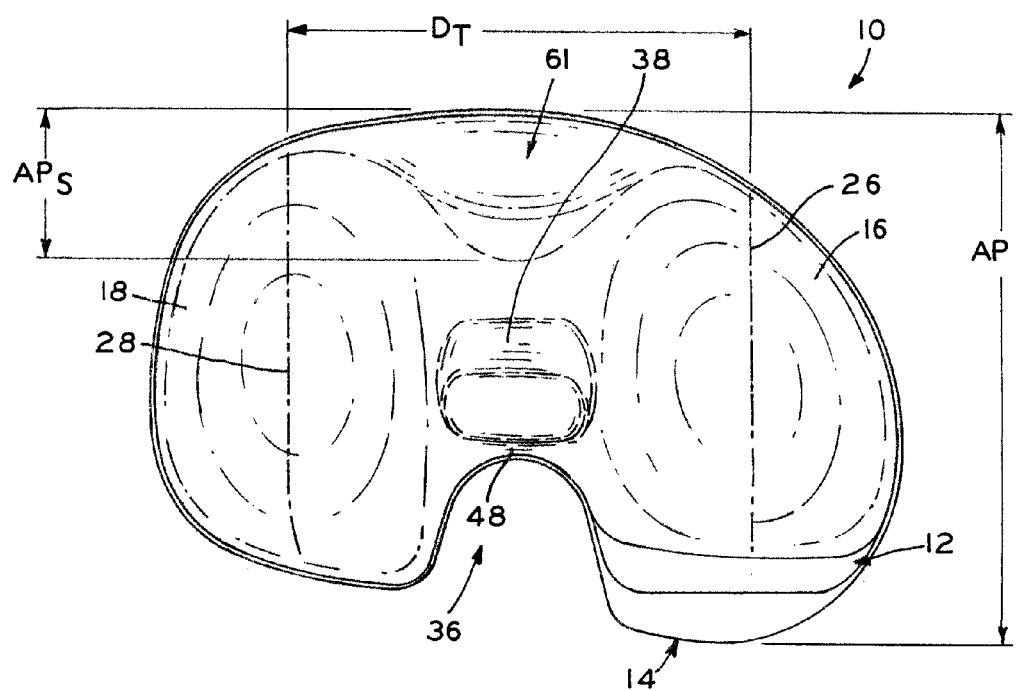
FIG. 11 is a top plan view of the tibial bearing component shown in FIG. 10.
Figure 12:
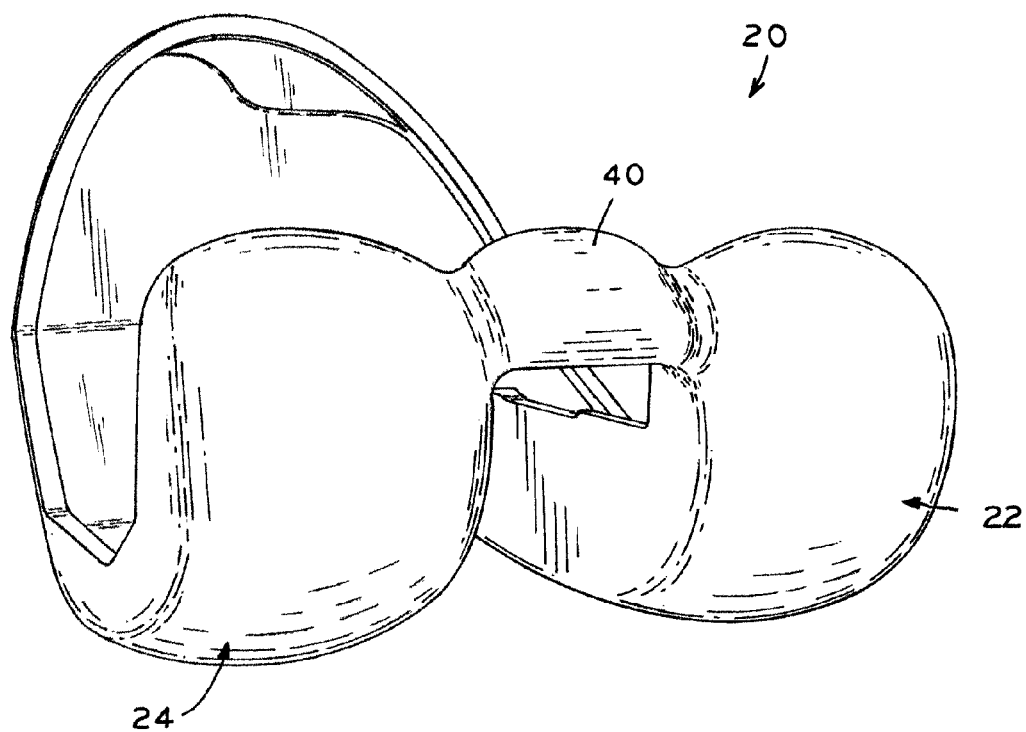
FIG. 12 is a perspective view of a posterior-stabilized femoral component in accordance with the present disclosure.

It is also contemplated that prosthesis designs in accordance with the present disclosure may include posterior stabilized (PS) prostheses and mid level constraint (MLC) prostheses, each of which includes tibial component 12 having spine 38 (FIGS. 10 and 11) and femoral component 20 having cam 40 (FIG. 12). Spine 38 and cam 40 are designed to cooperate with one another to stabilize femoral component 20 with respect to tibial bearing component 12 in lieu of a resected posterior cruciate ligament (PCL). For purposes of the present disclosure, PS and MLC prostheses are both considered to be "posterior-stabilized" designs including spine 38 extending proximally from the articular surface, in which the spine is spaced posteriorly from an anterior edge of the periphery of tibial bearing component 12 (FIGS. 10 and 11). Similar to intercondylar ridge 238 discussed above, spine 38 is disposed between medial and lateral dished articular compartments 16, 18.

Tibial bearing components 12, 212 include anterior relief spaces 61, 261, respectively, which are sagittally convex and therefore operate to protect and accommodate soft tissues of the knee during flexion, as described in detail below.

For simplicity, a cruciate-retaining (CR) type tibial bearing component 212 is shown in FIGS. 1-9 and described below to illustrate the features and geometry of anterior relief space 261. However, as noted above, anterior relief space 61 may be formed on posterior-stabilized tibial bearing component 12, or on any tibial bearing component for a knee. Tibial bearing component 212 is substantially similar to tibial bearing component 12 described above, with reference numerals of component 212 analogous to the reference numerals used in component 12, except with 200 added thereto. Structures of tibial bearing component 212 correspond to similar structures denoted by corresponding reference numerals of tibial bearing component 12, except as otherwise noted.

Bearing component 212 includes medial articular compartment 216 and lateral articular compartment 218, each defining concave dished articular surfaces sized and shaped to articulate with medial and lateral femoral condyles 222, 224, respectively, of femoral component 220 (FIG. 7) through a range of flexion to mimic the articulation of a natural knee. In one exemplary embodiment, the range of flexion may be from full extension (as shown in FIG. 9) to high flexion, such as 130 degrees or more. It is contemplated, however, that in some instances a tibial bearing component made in accordance with the present disclosure may articulate with the natural condyles of a patient's knee.

For purposes of the present disclosure, a central sagittal plane may be said to bisect tibial bearing component 12 into a medial portion including medial articular compartment 16 and a lateral portion including lateral compartment 18.

Figure 1:
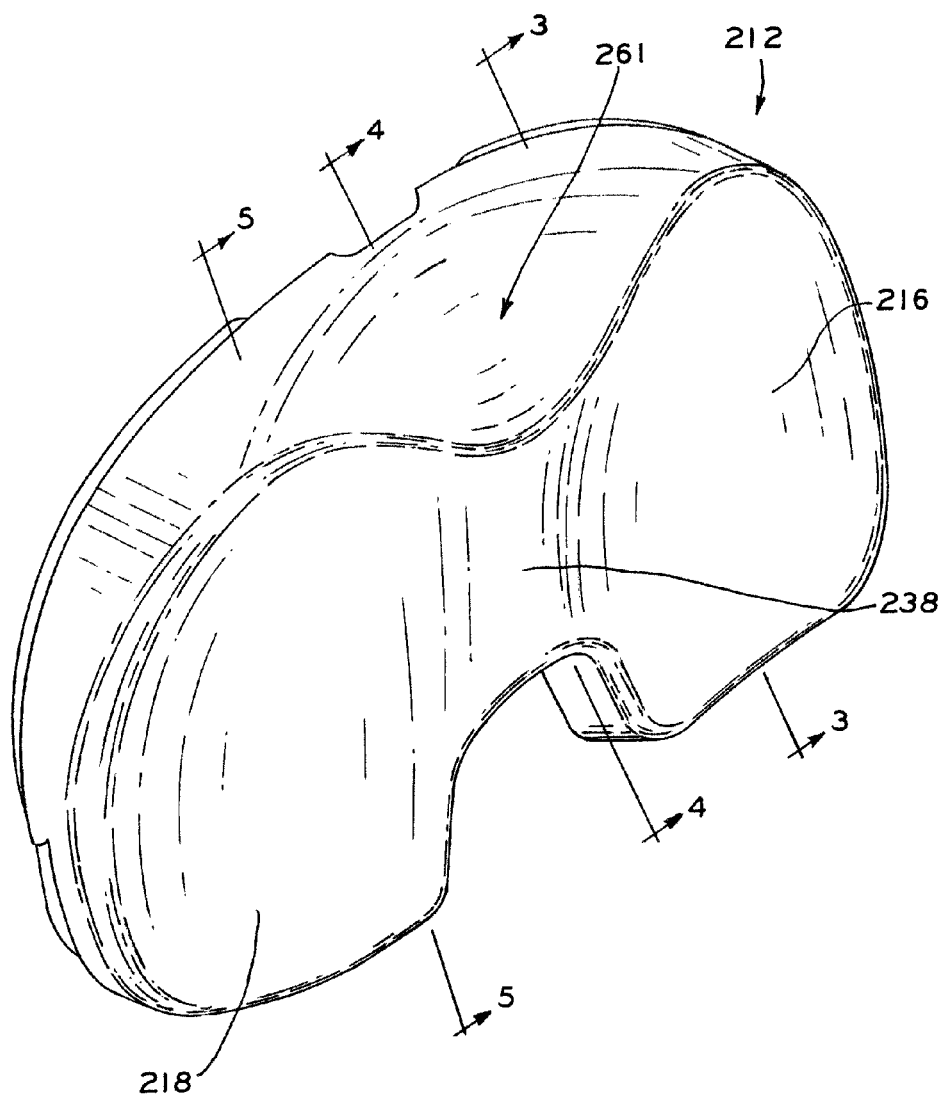
FIG. 1 is a top, perspective view of a cruciate-retaining (CR) tibial bearing component made in accordance with the present disclosure.
Figure 2:
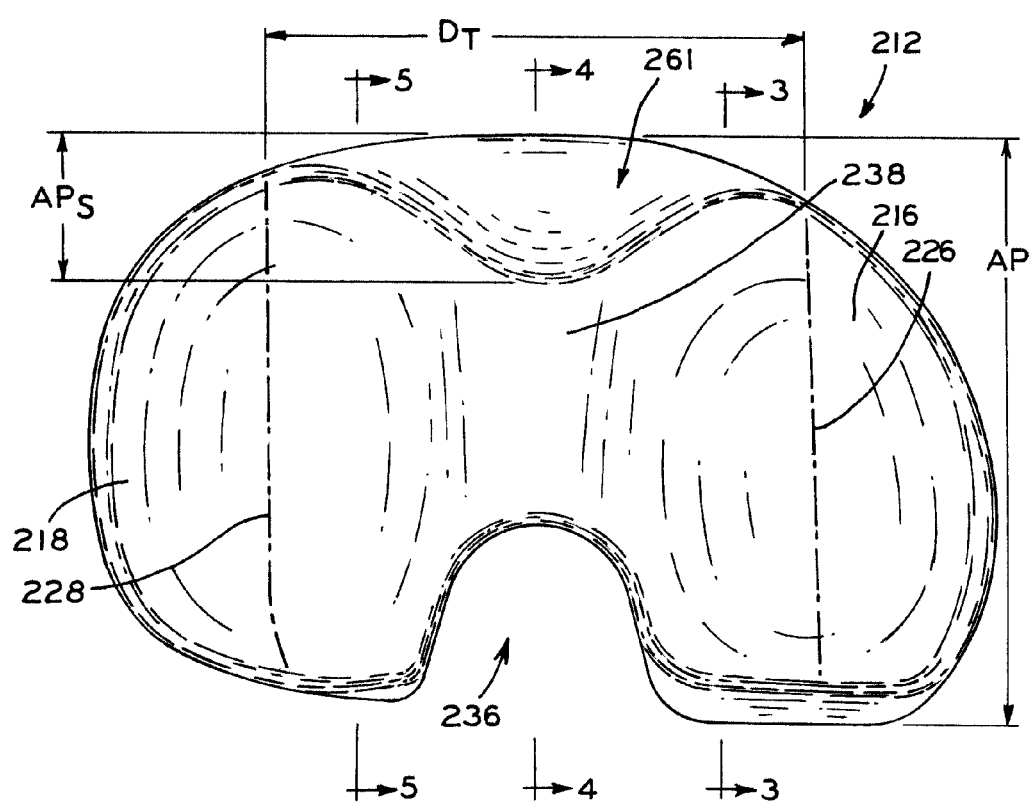
FIG. 2 is a top plan view of the tibial bearing component shown in FIG. 1.

During articulation from knee extension to flexion, the contact point between femoral condyles 222, 224 and articular compartments 216, 218 moves posteriorly, thereby defining medial articular track 226 and lateral articular track 228, respectively as shown in FIG. 2. Articular tracks 226, 228 are also representative of the lowest points along the anterior/posterior extent of medial and lateral articular compartments 16, 18.

Anterior relief space 261 is disposed at a generally anterior and central location on the proximal articular surface of tibial bearing component 212. Thus, relief space is positioned between medial and lateral articular compartments 216, 218, and between the anterior end of intercompartmental ridge 238 and the anterior peripheral edge of tibial bearing component 212.

Anterior relief space 261 defines sagittal convexity across its medial/lateral span, thereby accommodating soft tissues of the knee which may come into contact with this area during articulation of the knee prosthesis. The medial/lateral span may vary as required or desired for a particular application. In the illustrative embodiments of FIG. 2, the medial/lateral span is approximately equal to the distance $D_T$ between medial and lateral articular tracks 226, 228. Similarly, for the posterior stabilized-embodiment of FIG. 11 (discussed below), the medial/lateral span is approximately equal to the distance $D_T$ between medial and lateral articular tracks 26, 28.

Turning to FIG. 2, the anterior/posterior and medial/lateral bounds of anterior relief space 261 are illustrated. Relief space 261 sits between medial and lateral articular tracks 226, 228, and defines an anteroposterior extent $AP_S$ which is less than half of the overall anteroposterior extent of tibial bearing component 212. In an exemplary embodiment, anteroposterior extent $AP_S$ ranges from 8.8 mm to 14.1 mm. Moreover, anterior relief space 261 grows relatively larger as the overall size of tibial bearing component 212 grows larger across a family of nominal tibial prosthesis sizes. Across a range of prosthesis sizes, exemplary embodiments of anterior relief space 261 each define a respective anteroposterior extent $AP_S$ that is equal to between 10% and 30% of overall anterior/posterior extent AP of the tibial bearing periphery.

Figure 3:
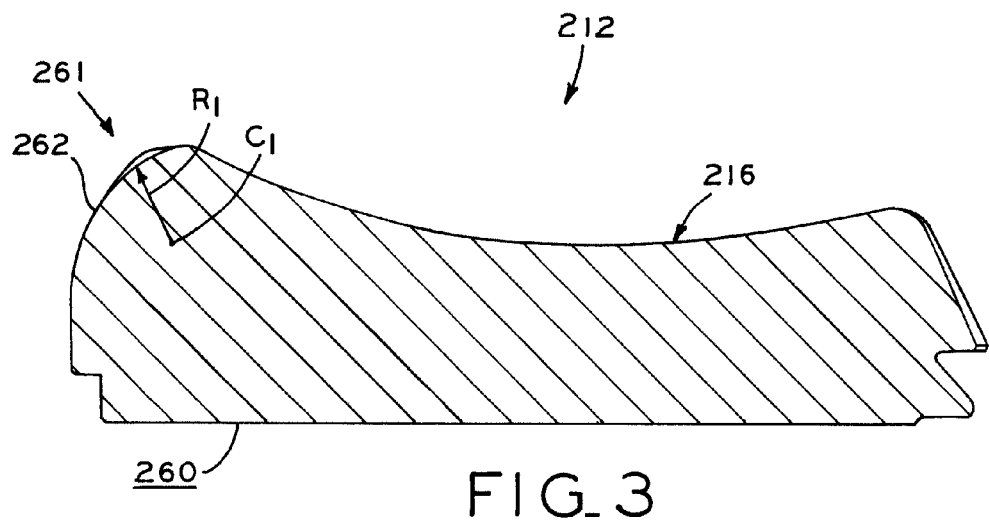
FIG. 3 is an elevation, cross-sectional view of the tibial bearing component shown in FIG. 1, taken along the line 3-3 of FIGS. 1 and 2.

Turning now to FIG. 3, a cross-section illustrating a medial portion of anterior relief space 261 is shown. As illustrated, this medial portion defines a sagittally convex profile 262 with a relatively small radius of curvature $R_1$ having center $C_1$ which is located distal and posterior of profile 262, i.e., profile 262 defines a convex curvature in the sagittal view of FIG. 3. As illustrated, the convex curvature of profile 262 extends across the entirety of the anterior/posterior extent of relief space 261, it being understood that such anterior/posterior extent is defined in a sagittal plane at the medial/lateral location of medial profile 262. Thus, it may be said that no portion of the anterior/posterior extent of medial profile 262 is flat or concave. In an exemplary embodiment, radius of curvature $R_1$ may be as small as 6 mm.

Figure 4:
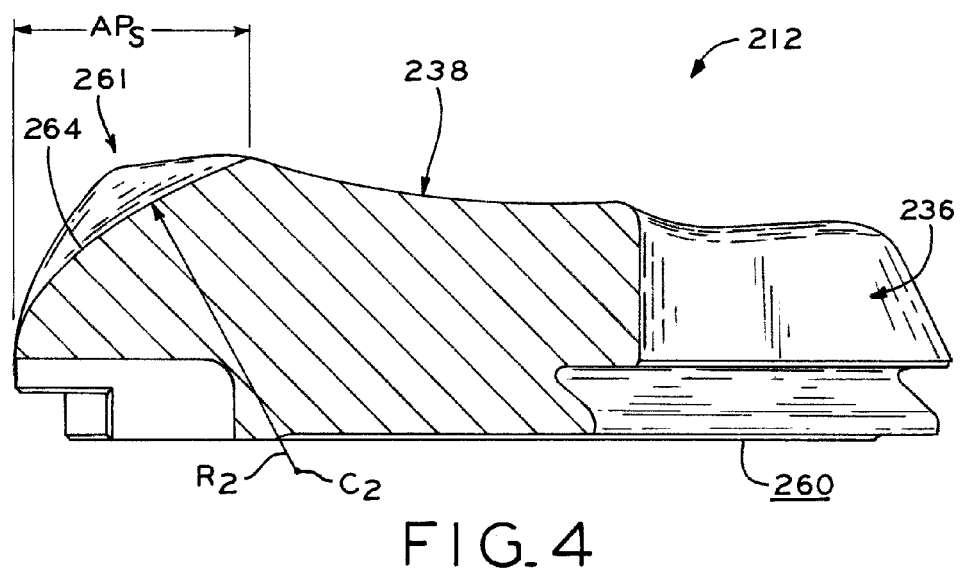
FIG. 4 is another elevation, cross-sectional view of the tibial bearing component shown in FIG. 1, taken along the line 4-4 of FIGS. 1 and 2.

FIG. 4 is another cross-sectional profile of anterior relief space 261, this time taken in the sagittal plane bisecting tibial bearing component 212 (as noted above). In the illustrative embodiment, the bisecting plane of FIG. 4 also bisects intercompartmental ridge 238 and anterior relief space 261 into substantially identical medial and lateral halves. At this central location, relief space 261 defines central curvature profile 264. Profile 264 defines radius of curvature $R_2$ which is substantially larger than radius $R_1$ of medial curvature profile 262. However, center $C_2$ of radius $R_2$ is also posterior and distal of central curvature profile 264, such that profile 264 is also convex in the sagittal view of FIG. 4. Similar to medial profile 262 described above, the convex curvature of central profile 264 extends across the entirety of the anterior/posterior extent of relief space 261, it being understood that such anterior/posterior extent is defined in a sagittal plane at the medial/lateral location of profile 264. Thus, no portion of the anterior/posterior extent of central profile 264 is flat or concave.

The medial/lateral positioning of central profile 264 may coincide with the largest anterior/posterior extent of anterior relief space 261, such that the entirety of the anterior/posterior extent of relief space 261 is equal to anterior/posterior extent $AP_S$ at central profile 264, as shown in FIG. 4. In an exemplary embodiment, radius of curvature $R_2$ is as little as 5 mm, 8 mm or 12 mm and as large as 35 mm, 48 mm or 50 mm, or may be any value within any range defined by any of the foregoing radius values.

FIG. 5 illustrates anterior relief space 261 via a cross-section taken near the lateral end thereof, where relief space 261 defines lateral curvature profile 266. Lateral curvature profile 266 defines radius $R_3$ having center $C_3$, in which center $C_3$ is distal and posterior of profile 266 to define a convex profile in a similar fashion as profiles 262, 264 described above. Radius $R_3$ is relatively smaller than radius $R_2$, and is comparable in magnitude to radius $R_1$. Similar to medial and central profiles 262, 264 described above, the convex curvature of lateral profile 266 extends across the entirety of the anterior/posterior extent of relief space 261, it being understood that such anterior/posterior extent is defined in a sagittal plane at the medial/lateral location of profile 266 in similar fashion to profiles 262, 264 described above. Thus, similar to profiles 262, 264, no portion of the anterior/posterior extent of lateral profile 266 is flat or concave. In an exemplary embodiment, radius of curvature $R_3$ may be as small as 9.8 mm.

In the above-mentioned exemplary family of nominal tibial prosthesis sizes, radii $R_1$, $R_2$ and $R_3$ are variable in proportion to the nominal prosthesis size. Thus, small prosthesis sizes define relatively smaller values for radii $R_1$, $R_2$ and $R_3$ respectively, and larger sizes define larger values for radii $R_1$, $R_2$ and $R_3$ respectively.

Medial, central and lateral profiles 262, 264, 266 have been chosen to illustrate the sagittal convexity of anterior relief space 261 at three discrete but representative medial/lateral cross-sections. However, it should be appreciated that each and every cross-section taken through anterior relief space 261 at any location along the medial/lateral extent of anterior relief space 261 would reveal similarly convex sagittal curvature profiles. Advantageously, this sagittal convexity presents a "soft" and rounded surface curvature which minimizes abrasive forces on adjacent soft tissues. In this way, anterior relief space 261 may be said to be "soft tissue friendly".

Turning to the coronal/transverse perspective of FIG. 6, relief space 261 defines a generally concave medial/lateral profile. This concave medial/lateral profile renders central profile 264 recessed with respect to medial and lateral profiles 262, 266, as can be seen by a comparison of FIG. 4 to FIGS. 3 and 5. More particularly, the outer surface of anterior relief space 261 at central profile 264 is posterior and distal of the outer surface at medial and lateral profiles 262, 266. This coronal/transverse concavity of anterior relief space 261 channels adjacent soft tissues into contact with the rounded, sagittally convex surfaces of anterior relief space 261, and away from the anterior edges of medial and lateral articular compartments 216, 218 which define relatively smaller radii and are therefore less soft-tissue friendly.

As noted above, anterior relief space 261 is illustrated as part of cruciate-retaining or ultra-congruent tibial bearing component 212, but may also be included in posterior-stabilized bearing component designs. FIG. 11 illustrates tibial prosthesis 10 having posterior-stabilized tibial bearing component 12 mounted to tibial baseplate 14. The perspective of FIG. 11 is a transverse-plane view of tibial prosthesis 10, looking down upon the proximally facing articular surface of bearing component 12, such that the distal surface of bearing component 12 (analogous to distal surface 260 of component 212, FIGS. 7 and 8) is substantially parallel to the transverse plane.

Tibial bearing component 12 includes spine 38 disposed between medial and lateral articular compartments 16, 18 in place of intercompartmental ridge 238. Spine 38 includes posterior surface 48 which is shaped to articulate with posterior cam 40 of femoral component 20 (FIG. 12) during flexion to provide posterior stability to the prosthesis in lieu of a resected PCL. Articular compartments 16, 18 may also be differently shaped, in order to provide appropriate articular characteristics when interacting with condyles 22, 24 of femoral component 20.

Anterior relief space 61 (FIGS. 10 and 11) is provided on posterior-stabilized tibial bearing component 12. Anterior relief space 61 is similar to anterior relief space 261, and may include all the features discussed above with respect to relief space 261. Moreover, the advantages of soft-tissue protection and deep-flexion enablement provided by the sagittal convexity and medial/lateral concavity of anterior relief space 261 are also provided by anterior relief space 61, as the same anterior, anatomic soft tissues are typically left in place after surgical implantation of either of tibial bearing components 12, 212.

Figure 13:
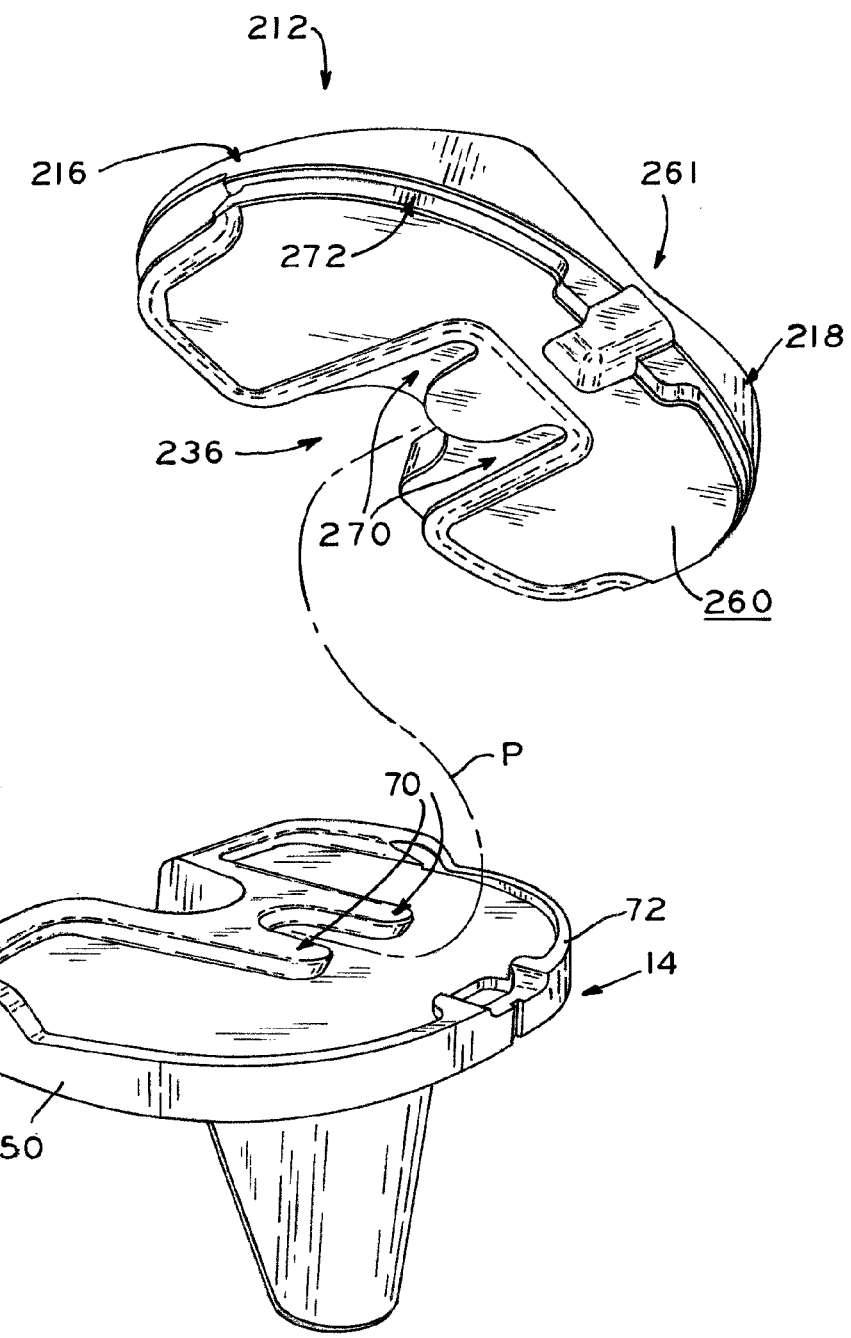
FIG. 13 is a perspective, exploded view of the tibial bearing component of FIG. 1, illustrating assembly thereof with a tibial baseplate made in accordance with the present disclosure.

In the exemplary embodiment described herein, tibial bearing components 12, 212 fixedly attach to tibial baseplate 14 (FIG. 11), such that tibial prosthesis 10 is said to be a "fixed-bearing" design. Referring to FIG. 13, distal surface 260 of tibial bearing component 212 includes a two-pronged recess 280 which cooperates with a correspondingly shaped two-prong boss 80 protruding proximally from tray 84 of tibial baseplate 14. Further, a peripheral undercut 282 formed around the periphery of distal surface 260 of tibial bearing component 212 is sized and shaped to receive peripheral wall 82. Upon assembly, tibial bearing component 212 is advanced along path P, such that tibial bearing component moves along a generally anterior-to-posterior path as recess 280 begins to engage with boss 80. Further posterior movement of tibial bearing component 212 causes a tight interfitting engagement between recess 280 and boss 80, and eventually aligns peripheral undercut 282 with peripheral wall 82. When so aligned, tibial bearing 212 "snaps" into fixed engagement with tibial baseplate 14. Posterior-stabilized tibial bearing component 12 may fixedly engage with tibial baseplate in a similar fashion.

Once such fixed engagement takes place, tibial bearing component 212 (or 12) is immovable with respect to tibial baseplate 14. As used herein, a "fixed bearing" tibial prosthesis is a prosthesis in which a bearing component is seated atop a tibial baseplate in a final, locked position such as the arrangement described above. In this locked position, lift-off of bearing components 12, 212 from tibial baseplate 14, as well as transverse movement of bearing components 12, 212 relative to tibial baseplate 14, is prevented during natural articulation of the knee. While some very small amount of motion (sometimes referred to as micromotion) may occur between tibial bearing components 12, 212 and tibial baseplate 14 in a fixed bearing prosthesis, no such motion occurs by design along a designated path.

Other types of fixed bearing prostheses include "monoblock" type designs, in which the tibial bearing component is permanently molded over the tibial baseplate to create a unitary tibial prosthesis. However, it is also contemplated that an anterior relief space in accordance with the present disclosure may be used on a "mobile bearing" prosthesis design in which the tibial bearing component is allowed to move relative to the tibial baseplate during articulation.

In order to prepare tibia T and femur F (FIG. 9) for receipt of a knee joint prosthesis of the present disclosure, any suitable methods or apparatuses for preparation of the knee joint may be used. Exemplary surgical procedures and associated surgical instruments are disclosed in "Zimmer LPS-Flex Fixed Bearing Knee, Surgical Technique", "NEXGEN COMPLETE KNEE SOLUTION, Surgical Technique for the CR-Flex Fixed Bearing Knee" and "Zimmer NexGen Complete Knee Solution Extramedullary/Intramedullary Tibial Resector, Surgical Technique" (collectively, the "Zimmer Surgical Techniques"), the entireties of which are hereby expressly incorporated herein by reference, copies of which are filed in an information disclosure statement on even date herewith.

While the present disclosure has been described as having exemplary designs, the present disclosure can be further modified within the spirit and scope of this disclosure. This application is therefore intended to cover any variations, uses or adaptations of the disclosure using its general principles. Further, this application is intended to cover such departures from the present disclosure as come within known or customary practice in the art to which this disclosure pertains.

What is claimed is:

1. A unitary tibial bearing component for articulation with femoral condyles, the tibial bearing component defining a tibial bearing component coordinate system comprising:

a bearing component transverse plane extending along a medial/lateral direction and an anterior/posterior direction;

a bearing component coronal plane extending along a proximal/distal direction and the medial/lateral direction, the bearing component coronal plane perpendicular to the bearing component transverse plane; and a bearing component sagittal plane extending along the anterior/posterior direction and the proximal/distal direction, the bearing component sagittal plane perpendicular to the bearing component transverse plane and the bearing component coronal plane, said tibial bearing component configured for connection to a tibial baseplate and comprising:

an articular surface and an opposing distal surface, said distal surface parallel to the bearing component transverse plane and sized and shaped for attachment to a proximal portion of the tibial baseplate, said articular surface including medial and lateral concave dished articular compartments sized and shaped for articulation with the femoral condyles, said medial and lateral dished articular compartments separated from one another by the bearing component sagittal plane, said articular and distal surface bounded by a tibial bearing periphery, an anterior relief space situated at a medial/lateral location between said medial and lateral dished articular compartments to define a medial/lateral span, said anterior relief space situated adjacent to an anterior edge of said tibial bearing periphery and extending posteriorly from said anterior edge across an anterior/posterior span, and said medial/lateral span of said anterior relief space comprising a plurality of sagittal cross-sectional profiles each extending from a posterior edge of said anterior relief space to an anterior edge of said anterior relief space, each of said plurality of sagittal cross-sectional profiles defining a convex sagittal curve extending from said posterior edge to said anterior edge of said anterior relief space.

2. The tibial bearing component of claim 1, wherein a coronal cross-section of said anterior relief space defines a concave medial/lateral profile.

3. The tibial bearing component of claim 1, wherein said anterior relief space defines an anterior/posterior relief space extent as measured in the bearing component transverse plane, said anterior/posterior relief space extent equal to between 10% and 30% of an overall anterior/posterior extent of said tibial bearing periphery.

4. The tibial bearing component of claim 3, wherein said convex sagittal curve of at least one of said plurality of sagittal cross-sectional profiles extends across an entirety of said anterior/posterior relief space extent.

5. The tibial bearing component of claim 1, wherein said convex sagittal curve defined by each of said plurality of sagittal cross-sectional profiles defines a radius of at least 5 mm.

6. The tibial bearing component of claim 1, wherein said convex sagittal curves of said plurality of sagittal cross-sectional profiles comprise a central curve on the bearing component sagittal plane, medial curves medial of said central curve, and lateral curves lateral of said central curve, said central curve defining a central curve radius, said medial and lateral curves defining a plurality of medial curve radii and a plurality of lateral curve radii, respectively, said central curve radius larger than said medial and lateral curve radii.

7. The tibial bearing component of claim 6, wherein said central curve radius is between 5 mm and 50 mm.

8. The tibial bearing component of claim 6, wherein said plurality of medial curve radii are as small as 9.8 mm.

9. The tibial bearing component of claim 6, wherein said plurality of lateral curve radii are as small as 6 mm.

10. The tibial bearing component of claim 1, wherein said medial/lateral span is approximately equal to a medial/lateral distance between a medial articular track and a lateral articular track defined by said medial and lateral dished articular compartments, respectively.

11. The tibial bearing component of claim 1, wherein said tibial bearing component comprises a posterior-stabilized design including a spine extending proximally from said articular surface, said spine spaced posteriorly from said anterior edge of said tibial bearing periphery, and said spine disposed between said medial and lateral dished articular compartments.

12. The tibial bearing component of claim 11, in combination with a femoral prosthesis wherein:
said femoral condyles comprising medial and lateral prosthetic condyles shaped to articulate with said medial and lateral dished articular compartments, respectively, through a flexion range, and
said femoral prosthesis includes a femoral cam positioned to articulate with said spine of said tibial bearing component when said femoral condyles articulate with said medial and lateral dished articular compartments.

13. The tibial bearing component of claim 1, wherein said tibial bearing component comprises one of an ultra-congruent design and a cruciate-retaining design comprising:
a posterior cutout sized and positioned to accommodate a posterior cruciate ligament upon implantation of said tibial bearing component; and
an intercondylar ridge extending anteroposteriorly from said posterior cutout to said anterior relief space, said intercondylar ridge disposed between said medial and lateral dished articular compartments.

14. The tibial bearing component of claim 13, in combination with a femoral prosthesis wherein:
said femoral condyles comprise medial and lateral prosthetic condyles shaped to articulate with said medial and lateral dished articular compartments, respectively, through a flexion range, and
said medial and lateral prosthetic condyles define an uninterrupted intercondylar space such that said femoral prosthesis lacks a femoral cam.

15. A unitary tibial bearing component for articulation with femoral condyles, the tibial bearing component defining a tibial bearing component coordinate system comprising:
a bearing component transverse plane extending along a medial/lateral direction and an anterior/posterior direction;
a bearing component coronal plane extending along a proximal/distal direction and the medial/lateral direction, the bearing component coronal plane perpendicular to the bearing component transverse plane; and
a bearing component sagittal plane extending along the anterior/posterior direction and the proximal/distal direction, the bearing component sagittal plane perpendicular to the bearing component transverse plane and the bearing component coronal plane,
said tibial bearing component configured for connection to a tibial baseplate and comprising:
an articular surface and an opposing distal surface, said distal surface parallel to the bearing component transverse plane and sized and shaped for attachment to a proximal portion of the tibial baseplate, said articular surface including medial and lateral concave dished articular compartments sized and shaped for articulation with the femoral condyles, said medial and lateral dished articular compartments separated from one another by the bearing component sagittal plane, said articular and distal surfaces bounded by a tibial bearing periphery,
an anterior relief space situated at a medial/lateral location between said medial and lateral dished articular compartments to define a medial/lateral span,
said anterior relief space situated adjacent to an anterior edge of said tibial bearing periphery and extending posteriorly from said anterior edge across an anterior/posterior span, and
said medial/lateral span of said anterior relief space comprising a plurality of sagittal cross-sectional profiles, each of said plurality of sagittal cross-sectional profiles defining a convex sagittal curve defining a sagittal curve radius of at least 5 mm.

16. The tibial bearing component of claim 15, wherein said anterior relief space defines an anterior/posterior relief space extent as measured in the bearing component transverse plane, said anterior/posterior relief space extent equal to between 10% and 30% of an overall anterior/posterior extent of said tibial bearing periphery.

17. The tibial bearing component of claim 15, wherein said convex sagittal curves of said plurality of sagittal cross-sectional profiles comprise a central curve on the bearing component sagittal plane, medial curves medial of said central curve, and lateral curves lateral of said central curve, said central curve defining a central curve radius, said medial and lateral curves defining a plurality of medial curve radii and a plurality of lateral curve radii, respectively, said central curve radius larger than said medial and lateral curve radii.

18. The tibial bearing component of claim 17, wherein said central curve radius is between 5 mm and 50 mm.

19. The tibial bearing component of claim 17, wherein said plurality of medial curve radii are as small as 9.8 mm.

20. The tibial bearing component of claim 17, wherein said plurality of lateral curve radii are as small as 6 mm.

21. The tibial bearing component of claim 15, wherein a coronal cross-section of said anterior relief space defines a concave medial/lateral profile.

22. A tibial bearing component for articulation with femoral condyles and comprising one of an ultra-congruent design and a cruciate-retaining design, the tibial bearing component defining a tibial bearing component coordinate system comprising:
a bearing component transverse plane extending along a medial/lateral direction and an anterior/posterior direction;
a bearing component coronal plane extending along a proximal/distal direction and the medial/lateral direction, the bearing component coronal plane perpendicular to the bearing component transverse plane; and
a bearing component sagittal plane extending along the anterior/posterior direction and the proximal/distal direction, the bearing component sagittal plane perpendicular to the bearing component transverse plane and the bearing component coronal plane,
said tibial bearing component comprising:
an articular surface and an opposing distal surface, said distal surface parallel to the bearing component transverse plane, said articular surface including medial and lateral dished articular compartments sized and shaped for articulation with the femoral condyles, said medial and lateral dished articular compartments separated from one another by the bearing component sagittal plane, said articular and distal surface bounded by a tibial bearing periphery;

an anterior relief space situated at a medial/lateral location between said medial and lateral dished articular compartments to define a medial/lateral span;

a posterior cutout sized and positioned to accommodate a posterior cruciate ligament upon implantation of said tibial bearing component; and an intercondylar ridge extending anteroposteriorly from said posterior cutout to said anterior relief space, said intercondylar ridge disposed between said medial and lateral dished articular compartments, said anterior relief space situated adjacent to an anterior edge of said tibial bearing periphery and extending posteriorly from said anterior edge across an anterior/posterior span, and said medial/lateral span of said anterior relief space comprising a plurality of sagittal cross-sectional profiles each extending from a posterior edge of said anterior relief space to an anterior edge of said anterior relief space, each of said plurality of sagittal cross-sectional profiles defining a convex sagittal curve extending from said posterior edge to said anterior edge of said anterior relief space.

23. The tibial bearing component of claim 22, in combination with a femoral prosthesis wherein:

said femoral condyles comprise medial and lateral prosthetic condyles shaped to articulate with said medial and lateral dished articular compartments, respectively, through a flexion range, and said medial and lateral prosthetic condyles define an uninterrupted intercondylar space such that said femoral prosthesis lacks a femoral cam.

* * * * *